United States Patent
Kheradvar et al.

(12) 
(10) Patent No.: US 11,369,784 B2
(45) Date of Patent: Jun. 28, 2022

(54) SYNCHRONIZING A PULSATILE CARDIAC ASSIST DEVICE WITH A PACEMAKER

(71) Applicant: THE REGENTS OF THE UNIVERSITY OF CALIFORNIA, Oakland, CA (US)

(72) Inventors: Arash Kheradvar, Irvine, CA (US); Ronald J. Hosmer, Mission Viejo, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 36 days.

(21) Appl. No.: 16/434,037

(22) Filed: Jun. 6, 2019

(65) Prior Publication Data
US 2019/0374693 A1 Dec. 12, 2019

Related U.S. Application Data

(60) Provisional application No. 62/850,447, filed on May 20, 2019, provisional application No. 62/681,530, filed on Jun. 6, 2018.

(51) Int. Cl.
| | | |
|---|---|---|
| *A61M 60/50* | (2021.01) |
| *A61N 1/362* | (2006.01) |
| *A61M 60/148* | (2021.01) |
| *A61B 5/318* | (2021.01) |
| *A61N 1/37* | (2006.01) |
| *A61B 5/021* | (2006.01) |
| *A61M 60/268* | (2021.01) |
| *A61M 60/274* | (2021.01) |
| *A61M 60/871* | (2021.01) |

(52) U.S. Cl.
CPC .......... *A61M 60/50* (2021.01); *A61M 60/148* (2021.01); *A61N 1/3629* (2017.08); *A61B 5/021* (2013.01); *A61B 5/318* (2021.01); *A61M 60/268* (2021.01); *A61M 60/274* (2021.01); *A61M 60/871* (2021.01); *A61M 2230/04* (2013.01); *A61N 1/3706* (2013.01)

(58) Field of Classification Search
CPC .. A61M 1/1086; A61M 1/122; A61M 1/1068; A61M 1/127; A61N 1/3706; A61N 1/368; A61H 31/004
See application file for complete search history.

(56) References Cited

U.S. PATENT DOCUMENTS

| | | | | |
|---|---|---|---|---|
| 5,879,375 A * | 3/1999 | Larson, Jr. | ........... | H02K 41/031 607/30 |
| 2006/0167334 A1* | 7/2006 | Anstadt | ................ | A61N 1/0587 600/17 |
| 2008/0046016 A1* | 2/2008 | Ben-David | ........ | A61N 1/36114 607/6 |
| 2009/0131740 A1* | 5/2009 | Gharib | ................ | A61M 60/148 600/17 |

(Continued)

*Primary Examiner* — Carl H Layno
*Assistant Examiner* — Aya Ziad Bakkar
(74) *Attorney, Agent, or Firm* — Nguyen Tarbet LLC

(57) ABSTRACT

Methods for synchronizing the actions of a pulsatile cardiac assist device with a dysfunctional heart using a cardiac pacemaker. Aspects include receiving a signal from the pacemaker and actuating the pulsatile cardiac assist device in response to the signal from the pacemaker to either help push blood out of the heart during systole or to help suck blood from the atria during diastole.

16 Claims, 7 Drawing Sheets

(56) References Cited

U.S. PATENT DOCUMENTS

2013/0110895 A1\* 5/2013 Valentino ................ G06F 7/588
　　　　　　　　　　　　　　　　　　　　708/255
2015/0057488 A1\* 2/2015 Yomtov ................ A61M 60/50
　　　　　　　　　　　　　　　　　　　　600/17

\* cited by examiner

SYNCHRONIZING A PULSATILE CARDIAC ASSIST DEVICE WITH A PACEMAKER

FIELD

Methods, systems and apparatus for safely synchronizing the function of a pulsatile cardiac assist device with a pacemaker.

BACKGROUND

Heart failure is a global pandemic affecting at least 26 million people worldwide, and population-based studies report that about 1-2% of people have heart failure. The worldwide economic cost of heart failure in 2012 was estimated at $108 Billion per year. According to the Centers for Disease Control and Prevention (CDC), in the United States alone, heart failure affects 5.7 million individuals and annually costs the nation over $30 billion, which includes the cost of health care services, medications, and missed days of work. Heart failure cost is set to grow to $69.7B by 2030 according to the American Heart Association (AHA) Heart Disease and Stroke Statistics (2018). Furthermore, heart failure costs within the seven key markets of the U.S., France, Germany, Italy, Spain, the U.K., and Japan is set to grow from $3.7 billion in 2016 to around $16.1 billion by 2026, per the GlobalData research and consulting firm. This represents an impressive compound annual growth rate (CAGR) of 15.7 percent. Patients with advanced-stage heart failure have been receiving ventricular assist devices (VADs), also known as mechanical circulatory support devices, in lieu of heart transplants due to limited organ availability.

In the U.S., from 1988 to 2019, a total of 72,893 hearts have been implanted. The estimated number of people in ACC/AHA stage-D or NYHA class IV is 150,000 to 250,000. The approximate annual number of heart transplants performed in the U.S. is approximately 2,100. The growing shortage of donor hearts precludes the chance of heart transplant for all who need one.

VADs are implantable mechanical pumps that help pump blood from the ventricles to the rest of body. They can offer survival rates superior to those of transplants, and with excellent quality of life, but come with risks and limitations. As blood circulates through the VAD, blood clots may form, which can lead to thromboembolic events, such as stroke or heart attack, or cause the VAD to stop working. Blood contact with a VAD requires patients to take blood-thinning medications to reduce blood clot risks, but blood thinners increase the risk of dangerous internal bleeding.

VADs must be surgically implanted by irreversibly modifying the heart. Therefore, device malfunction may lead to immediate death. Device malfunction is much broader than pump failure, and based upon the VAD type, occurs for a variety of components at different rates. Right heart failure may occur due to ventricular flow mismatch, if a Left VAD (LVAD), the most common type of VAD, is implanted. VADs alter the natural pulsatile blood flow pattern to continuous, which limits their long-term suitability due to hemodynamics problems. All current devices still require an external power source supplied via a percutaneous driveline. Driveline infections occur frequently because the driveline exit site creates a conduit for bacterial access. VADs' continuous assist requires a major power supply. Therefore, the batteries need frequent recharge.

VADs and heart assist devices come with complications, and among those, neurologic problems due to stroke are the most devastating complication. In spite of continued advancements in design and development of the VADs, thromboembolic events leading to stroke occur in 14-47% of VAD patients per year with 20% mortality rates at 12 months and 30% at 24 months for the current state-of-the-art continuous-flow VAD systems (Tsukui H, et al. "Cerebrovascular accidents in patients with a ventricular assist device" *The Journal of Thoracic and Cardiovascular Surgery* 134: 114-123; Kirklin J K, et al. "Fifth intermacs annual report: Risk factor analysis from more than 6,000 mechanical circulatory support patients" *The Journal of Heart and Lung Transplantation* 32:141-156). The main reason for thrombus formation is the blood contact with the VADs' and particularly associated with non-physiological flow patterns in the continuous-flow VAD systems. Eliminating the risk of stroke and other thromboembolic-related issues would benefit every patient with a cardiac assist device. As cardiac assist technology improves, more patients will be considered for this type of treatment either as bridge-to-transplant or destination therapy.

Current cardiac assist devices are typically electromechanical pumps for assisting cardiac circulation (FIG. 1). A new research report by Future Market Insights (on the World-Wide-Web at: futuremarketinsights.com/reports/cardiac-assist-devices-market) emphasizes a shifting scenario of the global market of cardiac assist devices based on the worldwide escalation of cardiovascular diseases. The report describes the market forecast during the study period 2017-2027 indicating that the global burden of cardiovascular diseases is expected to be around 29% of the total deaths. This has boosted the need for better cardiac assist devices. Infinium Global Research reports that the overall ventricular assist devices market is expected to reach a market valuation of over US$1.9 billion by the end of 2022, growing at a CAGR of 17.3% during the forecast period of 2016 to 2022 (see the World-Wide-Web at: businesswire.com/news/home/20170306006052/en/Global-1.9-Billion-Left-Ventricular-Assist-Device).

Overall, established reimbursements in Medicare and increase in advanced health care systems will boost global market demand for cardiac assist devices. The global market is perceiving an increase in the need for technologically-advanced equipment for health care industry. In the past few years, the demand for new cardiac assist devices have already started to rise as these devices facilitate approval for bridge to transplant, and are the life-line support for patients pursuing to either recover from or wait for a heart transplant. Further, the government has already increased funding for research and development initiatives in advanced medical treatment options, according to the report by Future Market Insights. These considerations are expected to fire up the growth of the global cardiac assist devices market during the period 2017-2027. Alternatively, established reimbursements on Medicare in many regions has helped the market's growth, particularly in the U.S, where Medicare covers reimbursement for cardiac assist devices procedures. This encouraging reimbursement scenario persuades patients to undergo such medical procedures.

However, there are growing concerns over the risks related to the use of cardiac assist devices that partially or completely replace the heart, and these concerns may hinder the growth of the global cardiac assist devices market. There are specific risks associated with the current family of cardiac assist devices. The most common adverse events include infection, thrombus formation, hemorrhage, conduction abnormalities, and suction events. Concerns were raised regarding a sharp increase in thromboembolism incidence in VAD patients as reported in two major studies published in the New England Journal of Medicine (Starling R C, et al. "Unexpected abrupt increase in left ventricular assist device thrombosis" *New England Journal of Medicine* 2014; 370: 33-40) and the Journal of Heart and Lung Transplantation (Kirklin J K, et al. "Interagency registry for mechanically assisted circulatory support (intermacs) analysis of pump thrombosis in the heartmate ii left ventricular assist device" *The Journal of Heart and Lung Transplantation* 33:12-22). These clinical data show that continuous flow VAD pumps have an even greater predisposition for thrombogenesis than previously thought. These adverse effects have led to major losses for the industry due to the major problems that occurred to the patients. For example, Medtronic received warning letters from the FDA due to the thrombus formation in their small MVAD device. Additionally, Abbott's Heart-Mate II has led to several adverse events in clinical trials, e.g., bleeding, cardiac arrhythmia, local infection and respiratory failure, giving a negative impression to health care professionals (see the World-Wide Web at: futuremarketinsights.com/reports/cardiac-assist-devices-market.

These situations have resulted in total product recall, thereby hampering the revenue growth of the global cardiac assist devices market.

All the current heart assist devices require patients to receive blood thinner to minimize the risk for thrombus formation, which is due to the blood contact with the VADs' and particularly associated with non-physiological flow patterns in the continuous-flow VAD systems. Eliminating the risk of stroke and other thromboembolic-related issues would benefit every patient with a cardiac assist device. The risks and limitations can be summarized as follows. As blood circulates through the VAD, blood clots may form, which can lead to stroke or heart attack, or cause the VAD to stop working. Blood contact with the VAD requires patients to take blood-thinning medications to reduce blood clot risks, but blood thinners increase the risk of dangerous internal bleeding. VADs must be surgically implanted by irreversibly modifying the heart. Therefore, device malfunction may lead to immediate death. Device malfunction is much broader than pump failure, and based upon the VAD type, occurs for a variety of components at different rates. Right heart failure may occur due to ventricular flow mismatch, if a Left VAD (LVAD), the most common type of VAD, is implanted. VADs alter the natural pulsatile blood flow pattern to continuous, which limits their long-term suitability due to hemodynamics problems. All current devices still require an external power source supplied via a percutaneous driveline. Driveline infections occur frequently because the driveline exit site creates a conduit for bacterial access. VADs' continuous assist requires a major power supply; therefore, the batteries need frequent recharging.

SUMMARY

We disclose methods for synchronizing the actions of a pulsatile cardiac assist device with a dysfunctional heart using a cardiac pacemaker.

Some aspects relate to a method of synchronizing a pulsatile cardiac assist device with a pacemaker including:
receiving a signal from the pacemaker, and
actuating the pulsatile cardiac assist device in response to the signal from the pacemaker to either help push blood out of the heart during systole or to help suck blood from the atria during diastole.

In some examples, the pulsatile cardiac assist device and the pacemaker are paired, wherein after performing the sensing and pacing functions, the pulsatile cardiac assist device receives and analyzes the pacemaker (PM) signal and begins a ventricular contraction cycle of the heart by a mechanical means.

In some examples, the pacemaker is a native heart pacemaker.

In some examples, the native heart pacemaker is a Sinoatrial node, an Atrioventricular node or a Purkinje fiber.

In some examples, a signal and/or programmed response from the pacemaker is sent to the pulsatile cardiac assist device to contract the heart, synchronized within signals representing electrical activities of the heart muscles.

In some examples, the pacemaker is an atrial pacemaker that is activated only when the intrinsic atrial rate falls below a preset level.

In some examples, synchronization of the pulsatile cardiac assist device is activated to contract when ventricular demand pacing occurs as a single pacemaker spike followed by a QRS complex that is wide, and resembles a ventricular beat.

In some examples, the pacemaker and pulsatile cardiac assist device are activated to deliver a stimulus only when an intrinsic ventricular rate falls below a predetermined lower limit and wherein pacemaker activity is suppressed when the intrinsic heart rate is faster.

In some examples, a pulse generator supplies impulses to implanted electrodes, either at a fixed rate or in a programmed pattern, the pulsatile cardiac assist device receives the same signal to activate ventricular contraction in synchrony with a pacing demand from the pacemaker.

In some examples, the pacemaker has a permanent lead anchored in the ventricle.

In some examples, atrioventricular (AV) conduction is normal and a sinoatrial node is at fault, and a pacing wire is placed in the right atrium.

In some examples, the heart is blocked by an atrioventricular block (AV block) or a second degree atrioventricular block.

In some examples, the pulsatile cardiac assist device synchronizes with a dual-chamber pacemaker to avoid dyssynchronization during mechanical contraction of the ventricle.

In some examples, the pacemaker pacing systems has two atrial leads, one in the right atrial appendage and the other either in the coronary sinus or at the ostium of the coronary sinus.

In some examples, a ventricular lead is placed in the right ventricle, either at the apex or at the outflow tract.

In some examples, the pacemaker has leads placed in the right atrium, the right ventricle and the left ventricle of the heart.

In some examples, the pulsatile cardiac assist device further synchronizes with an implantable cardioverter defibrillator (ICD) to provide mechanical ventricular contraction as required.

In some examples, a splitter allows electrical signal delay between the pacemaker and the pulsatile cardiac assist device to ensure that both the pacemaker and the pulsatile cardiac assist device are synchronized to avoid dyssynchronization while sending the signal to the intrinsic heart to initialize the patients cardiac cycle and to the pulsatile cardiac assist device to initiate a mechanical ventricular contraction.

In some examples, the pulsatile cardiac assist device is connected and synchronized with the pacemaker using an integrated system board that has multiple components integrated into a processing unit.

In some examples, the pulsatile cardiac assist device is connected and synchronized with the pacemaker using a non-integrated system that utilizes installable components and removable expansion cards.

In some examples, a ventricle of a heart is contracted.

In some examples, the cardiac assist device performs the ventricular contraction within the heart's V interval.

In some examples, the signal from the pacemaker is sent to the pulsatile cardiac assist device or a processing unit that controls the pulsatile cardiac assist device as an input signal to actuate the pulsatile cardiac assist device.

In some examples, the device is linked wirelessly or by a wire in a parallel circuit with a ventricular lead of the pacemaker.

In some examples, the wire is connected to an analog input pin on a controller.

In some examples, the pulsatile cardiac assist device has a circuit board configured to analyze the input signal, wherein if the input signal reaches a capture threshold, it sends an output signal to the motor of the pulsatile cardiac assist device to actuate it.

In some examples, the pulsatile cardiac assist device is actuated only when a pacing signal is sent from the pacemaker to the heart, to capture the ventricles.

In some examples, the pulsatile cardiac assist device is only actuated once per pacing signal.

In some examples, a circuit board in the pulsatile cardiac assist device receives one or more input from the heart and/or the pacemaker.

In some examples, the one or more input comprises heart rate.

In some examples, the circuit board creates outputs for how fast and/or how long the motor of the pulsatile assist device assists the heart, wherein the outputs result in a desired ejection fraction.

In some examples, heart rate is calculated by a programmable oscillator.

In some examples, the programmable oscillator calculates heart rate prior to an output pulse calculated by an output pulse generator.

In some examples, the output pulse comprises an electrical stimuli created and sent to the heart.

In some examples, a periodic motor contracts and expands the pulsatile cardiac assist device at a desired pace and speed.

In some examples, the pulsatile heart assist device is controlled by the pacemaker to accord with the pace of the native heart.

In some examples, the pacemaker synchronizes the heart to a new desired pace.

In some examples, the pulsatile cardiac assist device only assists the heart as needed.

In some examples, the pulsatile cardiac assist device continuously assists the heart.

DETAILED DESCRIPTION

Disclosed herein are methods for synchronizing the actions of a pulsatile cardiac assist device with a heart using a cardiac pacemaker.

Methodology for Synchronizing a Pulsatile Heart Assist Device with a Pacemaker

The methods disclosed herein synchronize a pulsatile heart assist-device with the native heart of a patient to ensure that the device helps the heart at both diastole and systole. With the device working properly, reduced ventricular function of the patient is compensated. This method eliminates the potential of dyssynchronization where the assist device could work against the heart at different cardiac phases.

These methods are used for pulsatile assist devices, e.g., in combination with a biventricular pacemaker. The pacemaker performs signal reading and processing of the heart's electrical signals. When the pacemaker deems it necessary to signal the ventricles to contract, this signal is also sent to the pulsatile assist device as an input signal to actuate the pulsatile assist device. In some aspects, the pulsatile cardiac assist device and pacemaker are paired such that, after performing the sensing and pacing functions, the pulsatile cardiac assist device receives and analyzes the pacemaker signal and begins a "second" ventricular contraction cycle of the heart via mechanical means. In one aspect, the device uses a wire linked in a parallel circuit with one of the ventricular leads of the pacemaker. This wire may be connected to an analog input pin on a controller. This input signal may be analyzed via a circuit board. If the input signal reaches a certain threshold known as the capture threshold, it sends an output signal to the motor of the pulsatile assist device to actuate it. The capture threshold is the minimum required voltage to stimulate cardiomyocytes to contract and is seen as a pacing spike on an ECG. The capture threshold varies per patient, and updates throughout the patient's lifetime as the impedance of the lead changes. The pulsatile assist device is actuated only when the correct pacing signal is sent to heart to capture the ventricles. Typically, the pulsatile assist device is only actuated once per pacing signal.

Figure 5:
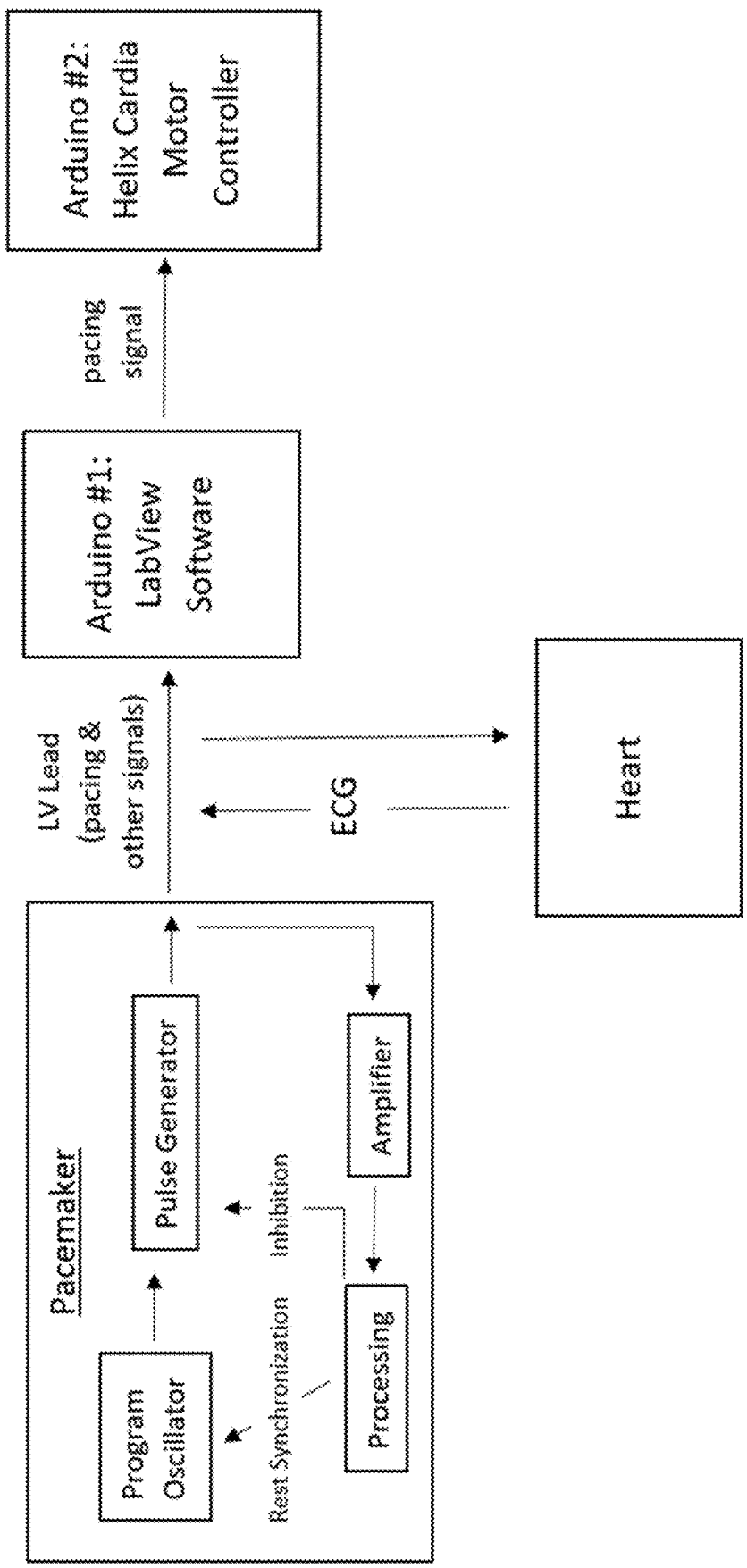
FIG. 5. Block diagram showing relationship between pacemaker, Arduino 1 and Arduino 2 and the heart.

A circuit board receives inputs from the heart and/or pacemaker, such as heart rate, and create outputs for how fast the motor of the pulsatile assist device will work and how long the pulsatile assist device will assist the heart. The heart rate is created by the "programmable oscillator" shown in the block diagram (FIG. 5). "Programmable oscillator" is calculated prior to "output pulse generator" and heart rate is calculated prior to electrical stimuli being created and sent to the heart. These outputs create the desired ejection fraction.

Steps for LabView and Arduino

How LabView Code "Analog Arduino Read Pin" works:

1. There are two Arduinos: one that has LabVIEW code uploaded (Arduino 1), and one that has Maxon Arduino code uploaded (Arduino 2).

Figure 6:
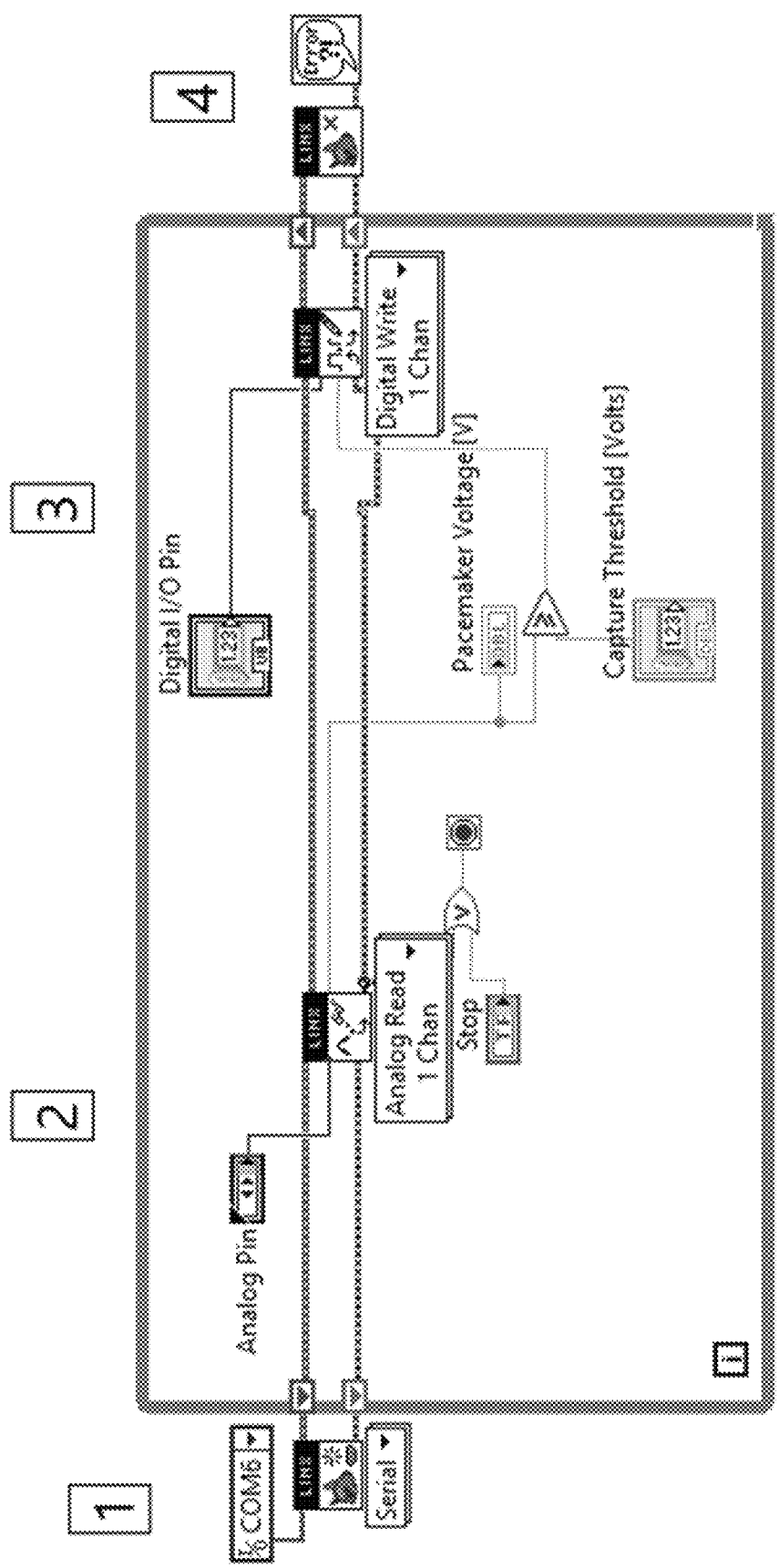
FIG. 6. Parallel circuit created by connecting a wire from the pacemaker's Left Ventricle lead to Arduino 1. Communication steps between pacemaker and Arduino 1 and Arduino 2: [1] Initialize connection to Arduino 1 by a default baud rate, e.g., 114200. [2] Read the specified analog input pin. [3] Compare voltage from left ventricle (LV) lead to Capture Threshold Voltage: (a) if [V]>Capture Threshold, the LV is being paced; (b) if [V]<Capture Threshold, the LV is not being paced. [4] Close connection to Aduino 1 and Arduino 2.

2. A parallel circuit is created by connecting a wire from the pacemaker's Left Ventricle lead to the Arduino 1 's analog read pin (pins A0-A5) (see FIG. 5 and FIG. 6). In the lab setting, an equivalent circuit is created by wiring the 5V pin on the Arduino 1 to a potentiometer (see FIG. 7, A), then wiring the output of the potentiometer to the Arduino 1's analog read pin (pins A0-A5). Any analog pin is fine; choose the same analog pin on the LabView Front Panel. Voltage output from pacemaker is read by the input pin on the Arduino.

Figure 7:
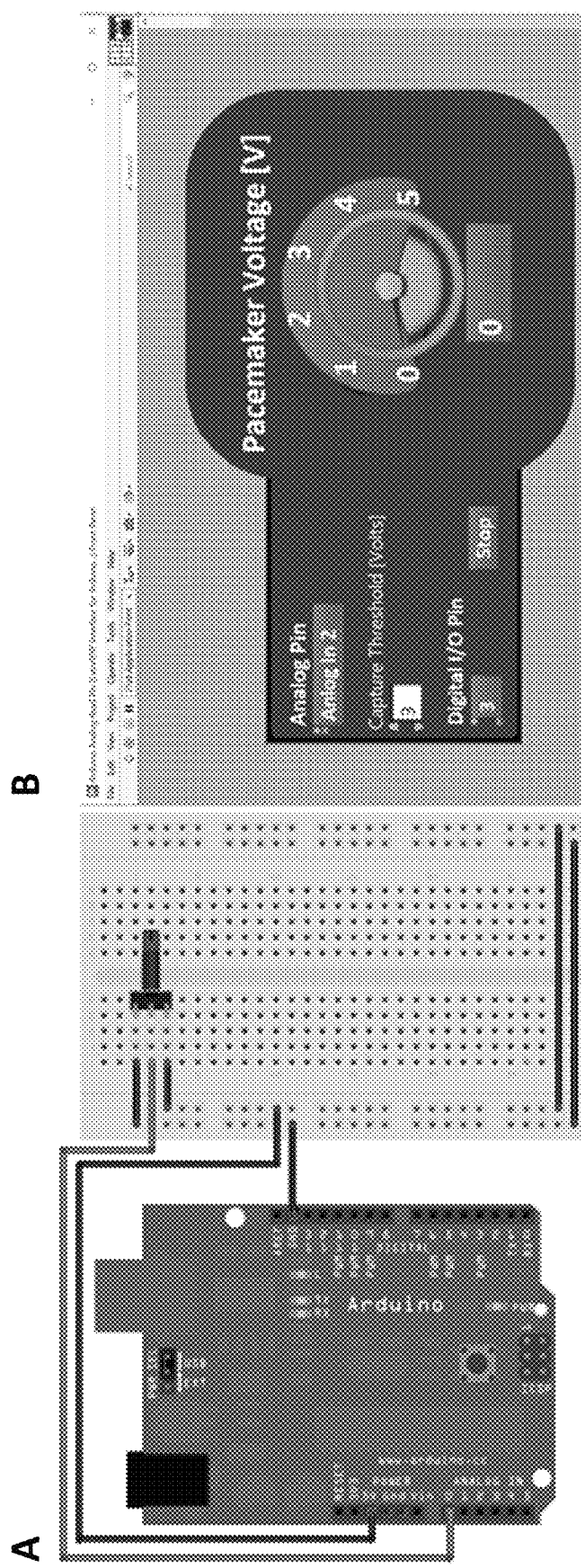
FIG. 7. (A) View of potentiometer. (B) View of LabView Code: Front Panel.

3. Voltage [V] (indicator) is measured and displayed on a Front Panel (FIG. 7, B). Voltage is compared to the Capture Threshold Voltage (control) set by the pacemaker's internal programming; for example, in the lab setting, we choose a voltage value between 0-5V on the Front Panel. The actual voltage output is controlled by the potentiometer. The T/F obtained is booled to I/O respectively and sends the I/O to the digital pin (pins 3-13). Connect the chosen digital pin on Arduino 1 to digital pin #2 on the Arduino 2; pin #2 can be changed within the Arduino code that is uploaded to this Arduino. Choose the desired digital pin on the Front Panel that matches the one used on the Arduino 1.

a. If [V]≥Capture Threshold Voltage, the Left Ventricle is being paced: for example, a 5V signal is sent to the output pin which is wired to the pulsatile heart-assist device, causing it to actuate.

b. If [V]<Capture Threshold Voltage, the Left Ventricle is not being paced: a 0V signal is sent to the pulsatile heart-assist device, causing nothing to occur.

4. All the Arduinos are grounded to the same ground port.

Whole-Heart Assist Device

The pulsatile heart assist device is a whole-heart assist device that wraps around the heart and assists in pumping function.

The pulsatile heart assist device is in the shape of a sleeve that externally wraps around the still-intact heart and provides an additional pumping force via contraction and expansion.

In some cases, the sleeve comprises of apical and basal structures that are interconnected to each other by helically-arranged fibers that are enclosed within the sleeve.

In some aspects, a periodic motor contracts and expands the sleeve at a desired pace and speed.

In some aspects, the pulsatile heart assist device is controlled by a pacemaker system to accord with the pace of the native heart.

In some aspects, a pacemaker system synchronizes the pumping system and the heart to a new desired pace.

In some aspects, the pulsatile heart assist device is powered by a percutaneously implanted power source that is wirelessly rechargeable over the skin.

In some aspects, wireless charging occurs via inductive charging, radio charging or resonance charging.

In some aspects, the pulsatile heart assist device is percutaneously implantable through a rib space.

In some aspects, the pulsatile heart assist device is surgically implantable.

In some aspects, the pulsatile heart assist device does not have any direct contact with circulating blood.

In some aspects, the pulsatile heart assist device only assists the heart as needed.

In some aspects, the pulsatile heart assist device continuously assists the heart.

In some aspects, the pulsatile heart assist device externally wraps over the pericardium of the still-intact-heart In some examples, the apical and basal structures comprise of an anchoring mechanism to the epicardial surface of the heart.

In some examples, the sleeve is made of a material, such as but not limited to fabric, PTFE, or elastomeric polymer.

In some aspects, the helically-arranged fibers are made of super-elastic material that enables fiber recoil.

In some aspects, the pulsatile heart assist device is externally anchored to a rib, the sternum or elsewhere within the thoracic cavity.

The pulsatile heart assist device is comprised of a conformal sleeve-shaped device that wraps around the heart and mechanically helps contract the heart to sync with the cardiac cycle. The device is empowered using motors similar to a micro-stepper motor that are implanted on the internal surface of the rib cage. The motor is connected to a battery that placed under the skin and is charged wirelessly. The pulsatile heart assist device is synchronized with the native heart via a pacemaker. The pulsatile heart assist device is ultimately implanted using a delivery system through intercostal space.

The pulsatile heart assist device patients do not need to take any blood thinning medications; therefore, the risk of dangerous internal bleeding is minimized. Implantation of the pulsatile heart assist device wraps the heart externally and does not modify the native heart. The pulsatile heart assist device avoids ventricular flow mismatch (dyssynchronization) through synchronizing with the native heart by a pacemaker. The pulsatile heart assist device provides normal pulsatile blood flow pattern. The pulsatile heart assist device is implanted within the internal surface of the rib cage and it will be connected to a battery that is under the skin and is charged wirelessly. This eliminates/reduces the risk of infections from the external sources. The pulsatile heart assist device works only on demand in conjunction with the pacemaker which conserves battery energy.

The pulsatile heart assist device avoids direct blood contact, as it naturally helps heart beat and therefore, patients do not require blood-thinning medications. Since the heart remains totally intact, the patient will not die even in case of device malfunction. The pulsatile heart assist device is implantable minimally-invasively through a small incision in the rib space, syncs with the heart via a pacemaker, and only assists the heart as needed. Therefore, it does not require continuous power supply, which makes it more power-efficient. A subcutaneous battery of the pulsatile heart assist device is wirelessly rechargeable, which eliminates the potential for driveline infection.

The pulsatile heart assist device is intended for use as Bridge-to-Transplant (BTT) and Destination Therapy (DT) for patients with advanced heart failure. The device is implantable through minimally-invasive surgery. Characteristics of the pulsatile heart assist device may include: (1) a heart-wrapping sleeve, (2) a superior conformal component, (3) an Apical conformal component, (4) a helically-shaped interconnecting fibers connecting the superior and apical portion, (5) a polyurethane sleeve that is in contact with the heart surface, (6) a miniature stepper motor that empower the sleeve to help assist the heart. The device is compatible with Commercial pacemakers and allows synchronization with the pacemaker. High-performance batteries that are based on lithium-iodine or lithium-manganese dioxide feature high volumetric energy densities and low self-discharge. They've been specifically designed for use in medical implants. In some embodiments, the device is rechargeable using wireless methods. The device has percutaneous drivelines that connect the motor to battery and the device provides pulsatile flow. In contrast, competitor devices include a continuous flow pump connecting to the surgically-modified heart, a large external power source and a driveline.

Advantageous designs are fully compatible with minimally-invasive surgical implantation of the device. Such as the motor will be implanted within the patients' chest cavity, and the battery will be wireless recharged. In contrast, current devices work based on continuous flow, which can lead to multiple complications. Also, existing technologies require and external drive and external battery sources, which lead to infection.

The device wraps around the heart, empowered by a miniaturized motor and battery. The device provides a minimal ejection fraction (EF) within a patients' normal range (50-70%). The battery can be rechargeable via external means (wireless). Components such as the body of the CAD, battery and drive motor are of a minimal size that can be implanted using minimally invasive means. All componentry are preferentially designed for internal implantation and no external hardware. In contrast, current devices have miniaturized their size but their mechanism of function is totally different. They require a larger battery than the pulsatile heart assist device. Competitive devices require external drive a battery sources which can lead to infection and potentially limit a patient's mobility.

Biocompatible polymers approved for use inside the body such as durable thermoplastic polyurethanes and nitinol wires for the Helix Cardia's heart sleeve are used. Regarding safety, all materials have previous biocompatible test results available, additional testing will be conducted as required. Materials are selected having a tested shelf life compatible with or beyond the expected life of the device. In contrast, current state-of-the-art VAD systems are made of titanium.

The device works in sync with the heart and Pacemaker to improve the ejection fraction to over 50% Required optimal torque to maintain proper contraction will be tested. Tests like tensile testing, fatigues testing etc. are performed on the parts. There is no minimal expectation. However, if the device stops working, it does not harm the patient because the patient's own heart still functions (although weakly).

Our device wraps around the heart and only assist the heart as needed. In a potential event that the device stops working, it will no additional harm to the patient as the native failing heart will be working and its function is not hampered by permanently modifying the heart the other technologies do.

To ensure that the device is always powered by the battery, will make sure that the patient receives sufficient notifications about the battery charge status. The chance for infection is minimal as the battery, device and drivelines are all implanted internally that minimizes the chance of infection.

In contrast, the current ventricular assist devices must be surgically implanted by irreversibly modifying the heart. Therefore, device malfunction may lead to immediate death. Device malfunction is much broader than pump failure, and based upon the VAD type, occurs for a variety of components at different rates. As blood circulates through the current VAD systems, blood clots may form, which can lead to stroke or heart attack, or cause the VAD to stop working. Blood contact with the VAD requires patients to take blood-thinning medications to reduce blood clot risks, but blood thinners increase the risk of dangerous internal bleeding. Right heart failure may occur due to ventricular flow mismatch, if a Left VAD (LVAD)—the most common type of VAD—is implanted. VADs alter the natural pulsatile blood flow pattern to continuous, which limits their long-term suitability due to hemodynamics problems. All current devices still require an external power source supplied via a percutaneous driveline. Driveline infections occur frequently because the driveline exit site creates a conduit for bacterial access. Also, driveline require special consideration for not to be bended/twisted or cut. VADs' continuous assist requires a major power supply; therefore, the batteries need frequent recharge. Outflow graft (the tube where the blood is sent to aorta from the end of motor) ruptures or tamponade on the graft are risk and can lead cardiac output to decrease.

Differentiation

Supporting a failing heart in patients with advanced heart failure has been the aim of devices developed as replacement therapy. Depending on the type of the support device, left, right or both ventricles can be assisted. More generally, assist devices can be grouped into either pulsatile or non-pulsatile based on their operational mechanism. The difference between the available two types are discussed in Rigatelli G, et al. "Past and present of cardiocirculatory assist devices: A comprehensive critical review" *Journal of Geriatric Cardiology JGC* 2012; 9:389-400, and are summarized in Table 1.

TABLE 1

Comparison between current pulsatile and continuous VADs

|  | Pulsatile | Continuous |
| --- | --- | --- |
| Size | Large | Smaller |
| Mechanism | Complex | Simpler |
| Control | Complex | Simpler |
| Valves | Two | None |
| Compliance | One | None |
| Implantability | Complex | Simpler |

TABLE 1-continued

Comparison between current pulsatile and continuous VADs

|  | Pulsatile | Continuous |
|---|---|---|
| Overall system | Same | Same |
| Cost | Higher | Lower |

It is common among all current devices that blood is removed from the dysfunctional ventricle into a pump and delivered to either aorta or pulmonary artery. Cardiac assist devices can be classified as total artificial heart (TAH) and ventricular assist devices (VADs), depending on their application. The first generation of the pumps were pulsatile, but they were large with multiple moving parts being implanted intracorporeally or para-corporeally. The second generation of pumps generates continuous flow and are miniaturized to have a single moving part, and therefore, they can be implanted intra-corporeally. The third generation of blood pumps use mechanical non-contact magnetic bearings and have been recently tested in clinical studies (Rigatelli G, et al. "Past and present of cardiocirculatory assist devices: A comprehensive critical review" *Journal of Geriatric Cardiology JGC* 2012; 9:389-400). Alternatively, the pulsatile heart assist device is a true "heart assist" device that externally wraps the heart to provide additional pumping force, and since this technology does not require direct blood contact, none of the concerns related to the traditional cardiac assist devices entail to this device.

All medical devices that are life supporting and are of considerable importance in preventing health impairment or may entail risk of injury or illness are considered class III medical devices. The most commonly used regulatory pathway for approval of the new class III medical devices in the U.S. is Pre-Market Application (PMA) pathway. The PMA pathway is appropriate for medical devices intended to treat congestive heart failure and its approval typically requires a large clinical study or randomized trial designed to demonstrate a reasonable assurance of safety and effectiveness (Almond C S. "The FDA review process for cardiac medical devices in children: A review for the clinician" *Progress in pediatric cardiology* 2012; 33:105-109). Examples of ventricular assist devices that have received PMA approval include the Heartmate II VAD for bridge-to-transplant.

Although the pulsatile heart assist device is significantly less invasive compared to the currently-available cardiac assist device technologies, it may still be considered a class III medical device since its implantation requires minimally invasive access to the mediastinum. However, once the pulsatile heart assist device is implanted and synchronized with the heart with a commercial pacemaker, it neither alters the heart structure nor has any direct contact with the blood. As well, if for whatever reason, the pulsatile heart assist device stops working, the heart function (although weak) will ensue and prevent sudden death, as is the case for the currently-available cardiac assist devices.

The pulsatile heart assist device may be used in patients requiring ventricular support due to end stage heart failure and bridge to transplant (BTT—short term use) patients awaiting cardiac transplantation as well as for destination therapy (DT—long term use), or patients who are not candidates for cardiac transplantation.

Product Profile

Figure 1:
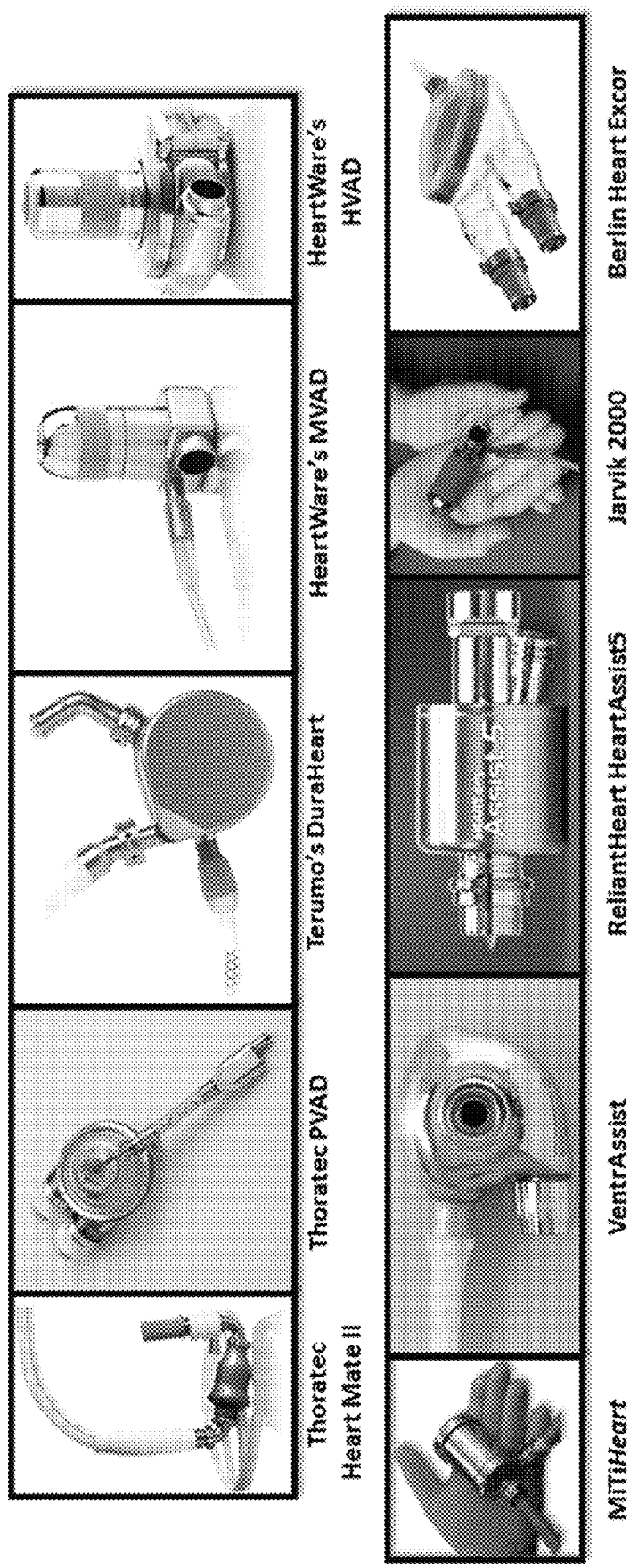
FIG. 1. Currently-available cardiac assist devices. A ventricular assist device (VAD) is a mechanical pump that is used to support cardiac function and blood flow in people with failing hearts. The device takes blood from a ventricle and helps pump it to the body.
Figure 2:
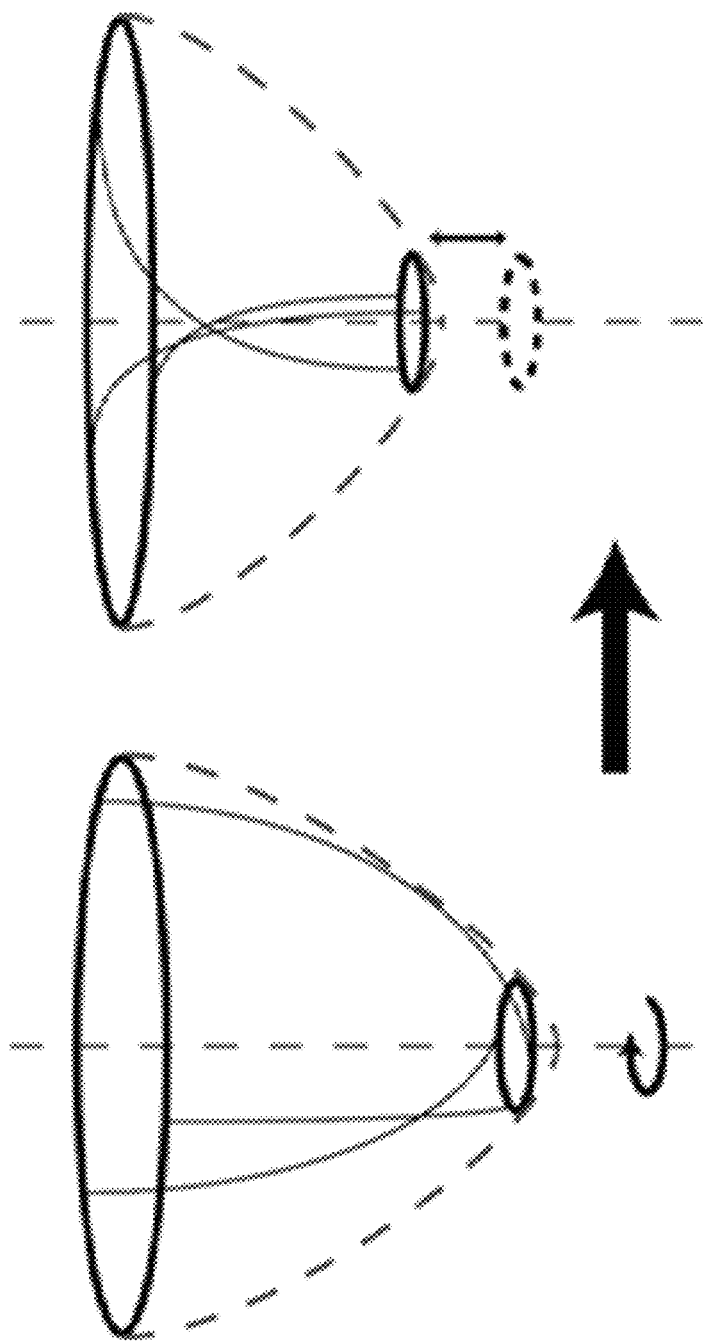
FIG. 2. The schematic diagram showing the basic mechanism on which the pulsatile heart assist-device works. The helical fibers that connect two rings to each other provide positive-displacement/suction pump, upon twisting the rings in opposite direction with respect to each other. Inspired by the natural myocardial contractile fibers, cyclic displacement of the helical fibers' orientation results in collapse or expansion of the chamber. Accordingly, a conformal chamber with inherent helical fibers wraps around the heart empowered by a cyclic stepper motor and provides assist to the heart. Red dashes demonstrate the border of the sac surrounding the rings/fibers (from U.S. Pat. No. 7,883,325 by Kheradvar et al.).

The pulsatile heart assist device is comprised of a conformal sleeve-shaped device that wraps around the heart and will mechanically help contract the heart to sync with the cardiac cycle. The sleeve deforms according to its patented helically-oriented fibers that provides additional contractile force to the heart (FIG. 2). The device is empowered using motors similar to a micro-stepper motor that will be implanted on the internal surface of the rib cage. The motor is connected to a battery that placed under the skin and is charged wirelessly. The pulsatile heart assist device is synchronized with the native heart via a commercially-available pacemaker. The pulsatile heart assist device may be implanted using a delivery system through intercostal space.

The device works based on the principle concept of helical fibers that connect two rings to each other provide positive-displacement/suction pump, upon twisting the rings in opposite direction with respect to each other. Inspired by the natural myocardial contractile fibers, cyclic displacement of the helical fibers' orientation results in collapse or expansion of the chamber. Accordingly, a conformal chamber with inherent helical fibers wraps around the heart empowered by a cyclic stepper motor and provides assist to the heart. More information of mechanism of action of the pulsatile heart assist device is provided in U.S. Pat. No. 7,883,325 by Kheradvar et al.

Features of the device include:

(1) The circulatory-isolated basis of the pulsatile heart assist device uniquely eliminates the blood contact and its related coagulopathy complications; thus, the device does not require the patient to take anticoagulant medications.

(2) The patented bio-inspired mechanism of the pulsatile heart assist device mimics the helical contraction of the cardiac myocardial fibers.

(3) The pulsatile heart assist device is controlled by a commercially-available pacemaker that also controls the heart rhythm ensuring that the pulsatile heart assist device is in harmony with the native heart. This ensures that the pulsatile heart assist device provides synergistic effect to stroke volume and prevents potential antagonist action to the heart.

(4) The pulsatile heart assist device is wrapped around and sutured to the pericardium using an adjustable strip and surgical felt rather than irreversibly changing the heart by tunneling the LV to aorta. Therefore, the pulsatile heart assist device only externally assists the heart and preserves the natural anatomy and physiology of the patient's heart. As well, if needed, the pulsatile heart assist device can be safely removed from the heart without major complications.

(5) Due to its conformal sleeve shape, the pulsatile heart assist device is implantable by minimally-invasive surgery via a left thoracotomy without the need for cardiopulmonary bypass.

Figure 3:
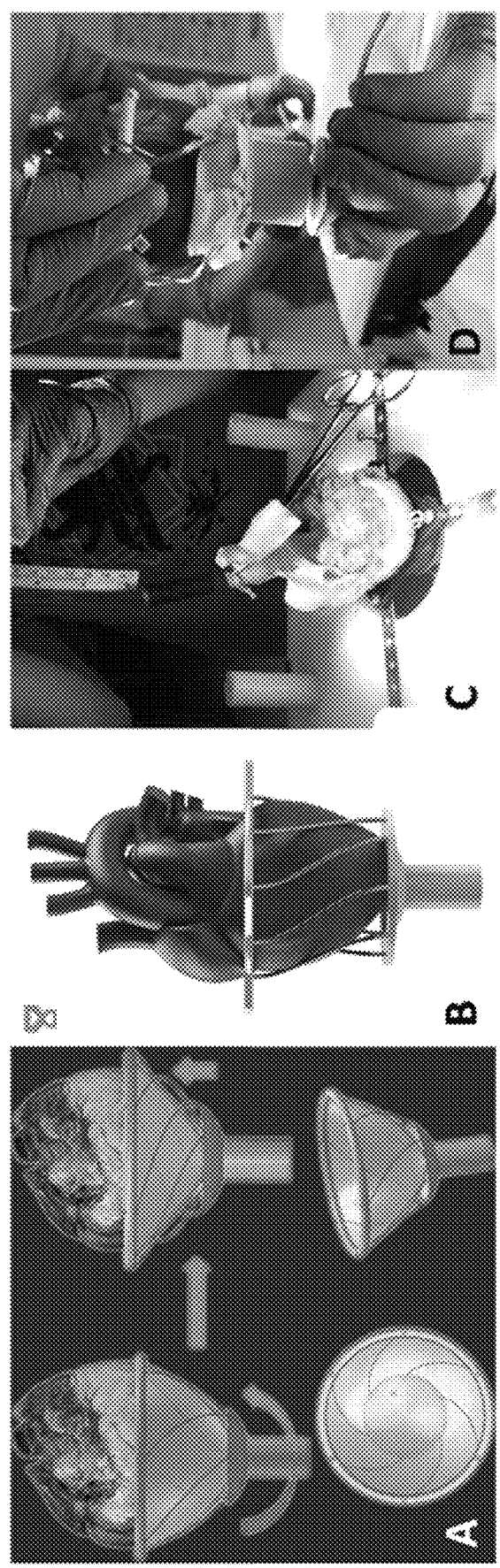
FIG. 3. (A) Schematic figure showing a pig heart in a conformal sleeve of pulsatile heart assist-device and how the helical fibers that connect two rings to each other provide positive-displacement/suction pump, upon twisting the rings in opposite direction with respect to each other. (B) pulsatile heart assist-device schematics. (C) Measuring the pulsatile heart assist-device's stroke volume in an ex-vivo experiment involving a pig heart. (D) Setting up another ex-vivo experiment using pig heart. The preliminary stepper motor of the pulsatile heart assist-device is shown.
Figure 4:
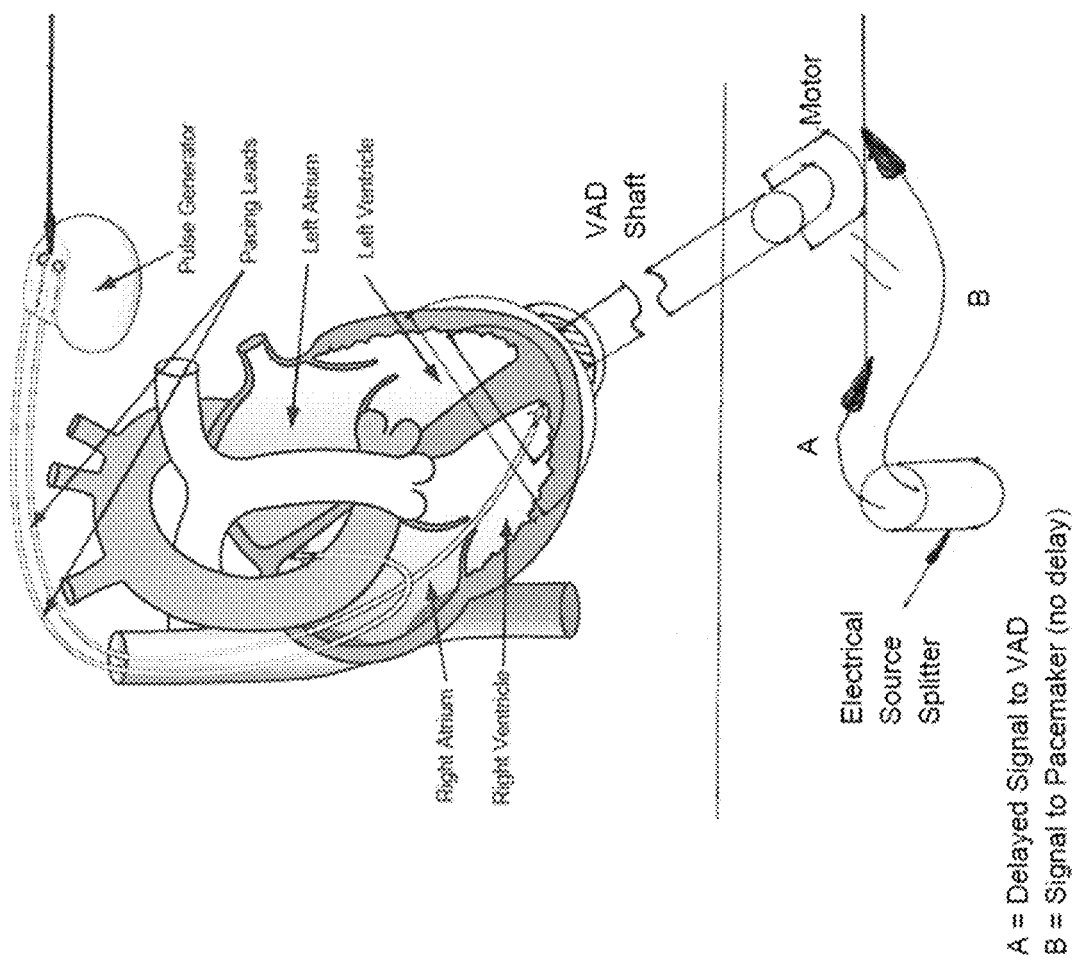
FIG. 4. Cardiac Assist Device (CAD), implanted with a heart and in communication with a pacemaker.

(6) The pulsatile heart assist device requires minimal energy input as it does not directly pumping fluid and only requires cyclic rotational motion of the apical ring with respect to its basal ring (FIGS. 2 and 3). Therefore, it does not require a large power supply.

(7) The pulsatile heart assist device uses a subcutaneous battery that is wirelessly rechargeable, which eliminates the potential for driveline infection.

Device attachment may be over the heart's epicardial surface or over the pericardial sac to result in the best outcome. The device's secure attachment, protection of the coronary vasculature and the device function are taken into consideration. The helical fiber orientation angle is optimized to generate the required additional stroke volume. In that regard, we have previously published a journal article on the effect of helical fiber geometry on pulsatile pumping and energy expenditure (Grosberg A, et al. "Effect of fiber geometry on pulsatile pumping and energy expenditure"

Bulletin of Mathematical Biology 2009; 71:1580). The same approach is followed optimize the design to maximize the heart assist effect and minimize the pump's energy expenditure. Synchronization of the pulsatile heart assist device with a pacemaker is a totally new concept and has not been practiced before.

In some embodiments, the synchronization method pertains to a helically-actuated device, such as described under U.S. Pat. Nos. 9,656,009, 8,794,937 and 7,883,325.

Other embodiments may include features described in U.S. Pat. No. 6,984,201, which relates to a blood circulation assistance device, U.S. Pat. No. 7,749,152, which relates to an impedance pump used in bypass grafts, U.S. Pat. No. 7,491,170, which discloses noninvasive methods for assessing valvular and ventricular dysfunction, and U.S. Pat. No. 7,524,298, which pertains to a device and related methods for treating hydrocephalus.

Resynchronization therapy may be useful for dyssynchrony in viable myocardium but has limitations when the myocardial tissue is non-contractile, as is often the case in patients suffering some sorts of cardiac dysfunction. Providing mechanical contractility assistance and synchrony in addition to correcting the electrical dyssynchrony may have great potential in improving heart function in these patients.

Our device is a true "heart assist" device that externally wraps the heart and provides an additional pumping force via a helically-arranged mechanism, which improves both types of heart function (i.e., systole and diastole). This technology does not require direct blood contact, and therefore, there is no need for blood-thinning medications. Since the heart remains totally intact, the patient will not die even in case of device malfunction. The pulsatile heart assist device is implantable minimally-invasively through a small incision in the rib space. It synchronizes with the heart via a pacemaker and only assists the heart as needed. Therefore, it does not require continuous power supply, which makes it more power-efficient. In some embodiments, a subcutaneous battery of the pulsatile heart assist device is wirelessly rechargeable, which eliminates the potential for driveline infection.

Some embodiments relate to a helically-actuated cardiac assist device, which is a single use, implantable medical device, and an insertion process thereof. The device Cardiac Assist Device (CAD) is intended for use as an assist to the whole heart function for a patient.

Also disclosed is a method of synchronizing a helically actuated CAD with a cardiac resynchronization therapy pacemaker.

Some embodiments relate to the ability of the cardiac assist device to synchronize with a pacemaker to avoid dyssynchronization while performing a mechanical ventricular contraction for heart failure patients when the electrical activity is inappropriately slow or absent. The action is to pair the cardiac assist device and Pace Maker such that after performing the sensing, and pacing functions, the cardiac assist device receives, analyzes the pacemaker (PM) signal which begins a "second" ventricular contraction cycle of the heart via mechanical means. The pacemaker can be the native heart's pacemakers such as Sinoatrial and Atrioventricular nodes or purkinje fibers.

A further benefit of the paring method with an artificial pace maker is that the cardiac assist device performs the ventricular contraction within the heart's V interval. The capability of the VAD to sync within the heart's V deflection ensures the PM pacing and cardiac assist device mechanical contractions are synced during ventricular activation.

The synchronization of the cardiac assist device and the cardiac pacemaker is to ensure the cardiac contraction safeguards that while In Systole and relaxation during diastole, the cardiac assist device works in conjunction within the rhythm of a failing heart and not against blood flow thus avoiding any desynchrony. The pacemaker signal activates the cardiac assist device to help push the blood out of the heart during systole and help suck the blood from atria during diastole.

Premature Ventricular Contraction (PVC):

A signal and/or programmed response from the PM is sent to the cardiac assist device to contract the heart in sync within the QRS complex pacing cycle.

In some embodiments, the method includes but is not limited to Implanted and Temporary Pacemakers and Implantable Cardioverter Defibrillators.

In some embodiments, the methods have an ability to synchronize and contract the ventricle of a failing heart within the Cardiac electrical activity (e.g., QRS complex) to ensure mechanical heart constrictions occur within the V-Deflection and do not disrupt the depolarization of the right and left ventricles.

Atrial Pacing Only:

The cardiac assist device's mechanical contraction synchronizes with and is dependent upon the location of the atrial lead which may be normal, diminutive, biphasic, or negative. In this case, mechanical atrial contractions synchronize along with a single atrial pacemaker stimulus followed by a P wave. This method includes intermittent captures when the atrial pacemaker is in a demand mode and is activated only when the intrinsic atrial rate falls below a preset level.

Ventricular Pacing Only:

Synchronization of the cardiac assist device's mechanical contraction occurs when Ventricular demand pacing occurs as a single pacemaker spike followed by a QRS complex that is wide, and resembles a ventricular beat (waveform 2). The pacemaker lead is usually in the right ventricular apex. Under this method, the paced QRS complex has a left bundle branch block (LBBB) configuration causing right ventricular activation before activation of the left ventricle. The mechanical contraction occurs within the QRS Complex to avoid ventricular dyssynchrony.

Single Chamber Pacing Only:

If intrinsic or native atrial activity is present with a single chamber ventricular-only pacemaker, it occurs at a rate that differs from the ventricular rate since it is dissociated from the QRS complex. Frequently, ventricular demand pacing is used in association with atrial fibrillation.

Ventricular Demand Pacing Only:

cardiac assist device Mechanical contractions synchronize with the PM during episodic pacing in patients who have a ventricular demand pacemaker. The pacemaker and cardiac assist device are activated to deliver a stimulus only when the intrinsic ventricular rate falls below a predetermined lower limit; and pacemaker activity is suppressed when the intrinsic heart rate is faster (ventricular inhibited). If the native rate is slow, there will be 100 percent ventricular pacing and cardiac assist device mechanical contractions when fusion or pseudo fusion beats if the pacemaker rate and intrinsic heart rate are nearly identical, and the native and paced QRS complex occur simultaneously.

Pulse Generator:

The cardiac assist device is synced to, and can respond to signals from the pulse generator which is the power source for an artificial pacemaker. When the pulse generator supplies impulses to the implanted electrodes, either at a fixed rate or in a programmed pattern, the cardiac assist device receives the same signal to activate the ventricular contraction in sync with the pacing demand from the pace maker.

Unipolar Pacemakers:

The cardiac assist device is synced with a cardiac pacemaker with one permanent lead anchored in the ventricle responding to patients in whom atrioventricular (AV block) conduction is likely to return; if the AV conduction is normal and sinoatrial node at fault, then the pacing wire is placed in the right atrium. There are three degrees of AV blockages the cardiac assist device can synchronize with. These include, first, second and third-degree blockages.

Atrioventricular Block (AV Block):

A type of heart block in which the conduction between the atria and ventricles of the heart is impaired. Under normal conditions, the sinoatrial node (SA node) in the atria sets the pace for the heart, and these impulses travel down to the ventricles. First-degree atrioventricular block—The heart's electrical signals move between the upper and lower chambers of the heart. PR interval greater than 0.20 sec.

Second-Degree Atrioventricular Block:

The heart's electrical signals between the upper and lower signals of the heart are slowed by a much greater rate than in first-degree atrioventricular block Third-degree atrioventricular block—No association between P waves and QRS complexes. The heart's electrical signals are slowed to a complete halt. This means that none of the signals reach either the upper or lower chambers causing a complete blockage of the ventricles and can result in cardiac arrest. Third-degree atrioventricular block is the most severe of the types of heart ventricle blockages Dual-Chamber Pacemaker:

Dual-chamber pacemakers generating electric impulses that are sent to the right atrium and right ventricle of the heart, thereby stimulating contractions and allowing the two chambers to maintain rhythm. The cardiac assist device will synchronize with a dual-chamber pace maker to avoid dyssynchronization during the mechanical contraction of the ventricle.

Dual-Site Atrial Pacing:

Newer pacing systems have two atrial leads, one in the right atrial appendage and the other either in the coronary sinus or at the ostium of the coronary sinus.

The ventricular lead is in the right ventricle, either at the apex or at the outflow tract. Studies show that there exist variations in the AV interval during atrial pacing that have significant effects on LA function. Because of altered atrial activation, the AV interval associated with optimal LA mechanical function during dual-site RA pacing was significantly shorter than that during RA pacing. This observation has important implications with respect to the programming of dual-site RA pacemakers implanted to prevent AF for hemodynamic purpose. In our case, we would trigger mechanical contractions off the signal from the LV lead but "may" need to evaluate and determine whether there is a need to establish our length of our mechanical contractions to ensure we shut down "if" the AV interval is out of whack.

Biventricular Pacemakers:

A cardiac pacemaker in which the leads are placed in the right atrium, right ventricle and left ventricle. Management of patients with heart failure with abnormal intraventricular conduction, e.g., left bundle branch block on ECG, resulting in deranged ventricular contraction or dyssynchrony. In biventricular pacing, a lead is used to deliver current directly to the left ventricle, in addition to those used to deliver current to the right atrium and ventricle, so that the ventricles can be induced to pump in synchrony.

Implantable cardioverter defibrillators (ICDs combined with internal defibrillator) ICDs detect and stop abnormal heartbeats (arrhythmias). The device continuously monitors patient heartbeat and delivers electrical pulses to restore a normal heart rhythm when necessary. Implantable cardioverter defibrillators (ICD) reduce patient risk of cardiac death if the lower chambers of the intrinsic heart (ventricles) go into a dangerous rhythm and stop beating effectively (cardiac arrest). The device also provides mitigation if there is a dangerously fast heartbeat (ventricular tachycardia) or a chaotic heartbeat (ventricular fibrillation). The cardiac assist device synchronizes with the ICD and will provide a mechanical ventricular contraction as required.

Power Source Splitter:

Splitter allows electrical signal delay between Pace Maker and cardiac assist device to ensure both the Pace Maker and the cardiac assist device are synchronized to avoid dyssynchronization while sending the signal to the intrinsic heart to initialize the patients cardiac cycle and to the cardiac assist device to initiate a mechanical ventricular contraction.

Integrated System:

The cardiac assist system can be connected and synchronized using an integrated system board that has multiple components integrated into the controller (CPU.)

Non-Integrated System:

The cardiac assist system can be connected and synchronized using a non-integrated system that utilizes installable components and expansion cards that are removeable for upgrades.

Advantages Over the Prior Art

Existing devices do not provide a means to link or synchronize with a cardiac pacemaker. Existing technologies would require a means and method to be connected to and synchronized with a cardiac pacemaker. In contrast, advantageous, stand-alone features of the disclosed cardiac assist devices include: (1) they connect to a cardiac pacemaker; (2) they receive and respond to signals from a cardiac pacemaker to synchronize ventricular motion, (3) they provide a ventricular response while In Systole, and (4) the cardiac assist device works in conjunction with the rhythm of a failing heart and not against blood flow. The assist device avoids direct blood contact, as it naturally helps heart beat and therefore, patients do not require blood-thinning medications. Since the heart remains totally intact, the patient will not die even in case of device malfunction. The pulsatile heart assist device (e.g., HELIX CARDIA) is implantable minimally-invasively through a small incision in the rib space, syncs with the heart via a pacemaker, and only assists the heart as needed. Therefore, it does not require continuous power supply, which makes it more power-efficient. In some embodiments, the subcutaneous battery of the pulsatile heart assist device is wirelessly rechargeable, which eliminates the potential for driveline infection.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method of synchronizing a pulsatile cardiac assist device with a pacemaker in a subject, the method comprising:
    receiving a signal from the atria by the pacemaker, and
    actuating the pulsatile cardiac assist device in response to the atrial signal to help push blood out of a heart during systole or to help suck blood from an atrium during diastole, wherein the pulsatile cardiac assist device comprises a heart-wrapping sleeve comprising an apical ring structure and a basal ring structure that are interconnected to each other by a plurality of non-overlapping, helically-arranged fibers enclosed within the sleeve, and an actuator that cyclically actuates the sleeve to contract and assist contraction of the heart according to the signal received from the atria.

2. The method according to claim 1, wherein the pulsatile cardiac assist device and the pacemaker are paired, wherein the pulsatile cardiac assist device receives and analyzes atrial signals and accordingly begins contraction of the pulsatile cardiac assist device to assist the heart by a mechanical means.

3. The method according to claim 1 wherein the pacemaker is a native heart Sinoatrial node, Atrioventricular (AV) node or a Purkinje fiber.

4. The method according to claim 1, wherein a signal or programed response from the atria is sent to the pulsatile cardiac assist device to help the heart contract, synchronized within signals representing electrical activities of the heart.

5. The method according to claim 1, wherein the cardiac assist device is activated by the pacemaker only when the intrinsic atrial rate falls below a preset level.

6. The method according to claim 1, wherein when a pulse generator supplies impulses to implanted electrodes, either at a fixed rate or in a programmed pattern, the pulsatile cardiac assist device receives the impulses to activate ventricular contraction in synchrony with a pacing demand from the atria.

7. The method according to claim 1, wherein the pacemaker has a permanent lead anchored in the atria.

8. The method according to claim 1, wherein atrioventricular (AV) conduction is normal and a sinoatrial node is at fault, and a pacing wire is placed in the right atrium.

9. The method according to claim 1, wherein the heart is blocked by an atrioventricular block (AV block) or a second-degree atrioventricular block.

10. The method according to claim 1, wherein the pulsatile cardiac assist device synchronizes with a dual-chamber pacemaker to avoid dyssynchronization during mechanical contraction of the ventricle.

11. The method according to claim 1, wherein the pacemaker receives signals from two atrial leads, one in the right atrial appendage and the other either in the coronary sinus or at the ostium of the coronary sinus.

12. The method according to claim 1, wherein the pacemaker has leads placed in the right atrium, the right ventricle and the left ventricle of the heart.

13. The method according to claim 1, wherein the pulsatile cardiac assist device further synchronizes with an implantable cardioverter defibrillator (ICD) to provide mechanical ventricular contraction as required.

14. The method according to claim 1, wherein a splitter allows electrical signal delay between the pacemaker and the pulsatile cardiac assist device to ensure that both the pacemaker and the pulsatile cardiac assist device are synchronized to avoid dyssynchronization while sending the signal to the intrinsic heart to initialize the patients cardiac cycle and to the pulsatile cardiac assist device to initiate a mechanical ventricular contraction.

15. The method according to claim 1, wherein the pulsatile cardiac assist device is connected and synchronized with the pacemaker using an integrated system board that has multiple components integrated into a processing unit.

16. The method according to claim 1, wherein the pulsatile cardiac assist device is connected and synchronized with the pacemaker using a non-integrated system that utilizes installable components and removable expansion cards.

* * * * *